United States Patent [19]

Inui

[11] Patent Number: 4,843,183

[45] Date of Patent: Jun. 27, 1989

[54] PROCESS FOR PRODUCING LOWER OLEFINIC HYDROCARBONS FROM METHANOL

[75] Inventor: Tomoyuki Inui, Kyoto, Japan

[73] Assignee: Showa Shell Sekiyu Kabushiki Kaisha, Tokyo, Japan

[21] Appl. No.: 75,612

[22] Filed: Jul. 20, 1987

Related U.S. Application Data

[63] Continuation-in-part of Ser. No. 30,297, Mar. 23, 1987, abandoned, which is a continuation of Ser. No. 762,955, Aug. 6, 1985, abandoned.

[30] Foreign Application Priority Data

Aug. 15, 1984 [JP] Japan ............................. 59-169368

[51] Int. Cl.$^4$ ............................................. C07C 1/22
[52] U.S. Cl. ................................... 585/640; 585/639; 585/642; 585/469; 585/732; 502/258; 502/259; 502/260; 502/164; 502/158; 502/61
[58] Field of Search ............... 585/640, 639, 642, 469, 585/732; 502/258, 259, 260, 164, 158, 61

[56] References Cited

U.S. PATENT DOCUMENTS

| | | | |
|---|---|---|---|
| 4,025,575 | 5/1977 | Chang et al. ........................ | 585/640 |
| 4,025,576 | 5/1977 | Chang et al. ........................ | 585/640 |
| 4,044,061 | 8/1977 | Chang et al. ........................ | 585/640 |
| 4,060,568 | 11/1977 | Rodeward ............................ | 585/640 |
| 4,371,628 | 2/1983 | Nanne et al. ........................ | 502/164 |
| 4,403,044 | 9/1983 | Post et al. ............................ | 585/640 |

FOREIGN PATENT DOCUMENTS 3215068 11/1982 Fed. Rep. of Germany ...... 502/164

OTHER PUBLICATIONS

Kirk Othmer, 3d Ed., vol. 15 pp. 638–642.

*Primary Examiner*—H. M. S. Sneed
*Assistant Examiner*—Chung K. Pak
*Attorney, Agent, or Firm*—Ladas & Parry

[57] ABSTRACT

Lower olefinic hydrocarbons are produced from methanol in a high yield and with a high selectivity by bringing methanol into contact with a metallosilicate catalyst of the formula Si/Me wherein atomic ratio of Si/Me is 25–3200 and Me is Fe, Ni or Co at a temperature of 250°–400° C., a space velocity of 2000–8000 hr$^{-1}$ and a pressure of atmospheric pressure −50 kg/cm$^2$.

14 Claims, No Drawings

PROCESS FOR PRODUCING LOWER OLEFINIC HYDROCARBONS FROM METHANOL

RELATED APPLICATIONS

This is a continuation-in-part of application Ser. No. 030,297 filed Mar. 23, 1987, now abandoned, which is a continuation of application Ser. No. 762,955 filed Aug. 6, 1985, now abandoned.

BACKGROUND OF THE INVENTION

This invention relates to a process for preparation of lower olefins from methanol.

More particularly, it relates to a process for preparation of lower olefins of 2 to 4 carbon atoms from methanol.

Indirect liquefaction method of coal and petrolium hydrocarbons via gasification has problems to be solved in efficiency of Fischer-Tropsch synthesis (FT synthesis) and selectivity to gasoline.

However, recently Mobil Oil Corp. has developed a technique to obtain olefins of $C_2$–$C_4$ carbon atoms from methanol using a novel zeolite catalyst with high selectivity, from which are expected novel composite catalysts and improved results by use of these catalysts for synthesis of lower hydrocarbons.

DE No. 3215068 (DISTILLERS) and U.S. Pat. No. 4,403,044 disclose production of olefinic hydrocarbons from methanol using a catalyst of alumina-free silicalite. However, said catalyst is not satisfactory in selectivity and yield of olefinic hydrocarbons.

SUMMARY OF THE INVENTION

The inventor has discovered a process for producing lower olefins ($C_2$–$C_4$ olefins) from methanol in high yield and with high selectivity in the presence of a metallosilicate catalyst (Si/Me wherein Me is Fe, Ni or Co).

It is an object of this invention to provide a process for producing lower olefins from methanol in a high yield and with a high selectivity.

DETAILED DESCRIPTION OF THE INVENTION

In accordance with this invention, methanol is brought into contact with a metallosilicate catalyst (Si/Me wherein atomic ratio of Si/Me is 25 to 3200 and Me is Fe, Ni or Co) under reaction conditions of a reaction temperature: 250° C. to 400° C., preferably 280° C. to 350° C., a space velocity (GHSV): 2000 to 8000 $hr^{-1}$ and a pressure: atmospheric pressure to 50 $kg/cm^2$.

The process of this invention is to produce lower olefins of $C_2$–$C_4$ carbon atoms from methanol at a high conversion and with a high selectivity.

Under conditions of a reaction temperature of lower than 250° C. and a space velocity (GHSV) of more than 8000 $hr^{-1}$, the conversion is liable to decrease, and under conditions of a reaction temperature of higher than 400° C. and a space velocity of less than 4000 $hr^{-1}$, decomposition products, mainly methane, and a gasoline component increase.

In order to keep high conversion and high selectivity, space velocity is small when reaction temperature is low, and large when reaction temperature is high.

Preparation of Catalyst (1) The first step of preparing a gel mixture:

Solution A: An aqueous solution containing a salt of metal (Me), i.e., a di- or tri-valent nitrate, sulfate or chloride and preferably nitrate of Fe, Ni or Co, a quaternary alkyl ammonium cation, and an inorganic acid of nitric, sulfuric or hydrochloric acid.

Preferable salts of a metal in the solution A are $Fe_2(SO_4)_3$, $CoSO_4$ and $NiSO_4$. The inorganic acid to be used has preferably the same anion as that of the metal salt above.

Solution B: An aqueous silicate solution.

Solution C: An aqueous solution of ion modifier (NaCl).

The solutions A and B are added to the solution C at a rate that pH of the solution C is kept at about 10, resulting to produce a gel mixture in the solution C.

An ion modifier of NaCl is added to the solution A and a quaternary alkyl ammonium cation with an inorganic acid and alkali hydroxide are added to the solution C at the time of the addition, in order to prevent each component in the solutions A, B and C from changing.

(2) The second step of grinding the resulting gel mixture.

(3) The third step of hydrothermal reaction:

The gel mixture is heated to a temperature from room temperature to 150°–190° C. at a constant speed followed by heating to 190°–220° C. at a constant speed or an exponential speed to obtain a precurser synthetic metalosilicate having the following chemical composition in molar ratio;

| | |
|---|---|
| Si/Me | 25–3200 |
| $OH^-/SiO_2$ | 0.3–1.0 |
| $H_2O/SiO_2$ | 30–100 |
| R/R + alkalimetal | 0.05–0.15 |
| $NaCl/H_2O$ | 0.01–0.06 |

Wherein
Me is Fe, Ni or Co,
R is a quaternary alkyl ammonium cation where alkyl is $C_{1-3}$ alkyl, and
alkali metal is sodium or potassium.

(4) The last fourth step is to calcine the precursor metalosilicate in (3).

Methanol in the gaseous form is brought into contact with a catalyst in a known manner.

| Preparation of, for instance, Fe-silicate (Si/Fe = 3200) Catalyst | |
|---|---|
| solution (A) | |
| $Fe(NO_3)_2$ $9H_2O$ | 0.04 g |
| $H_2SO_4$ | 6.2 g |
| TPAB* | 5.72 g |
| $H_2O$ | 60 cc |
| NaCl | 11.95 g |
| solution (B) | |
| $H_2O$ | 45 cc |
| Water Glass (No. 3)** | 69 g |
| solution (C) | |
| $H_2O$ | 208 cc |
| NaCl | 40.6 g |
| $H_2SO_4$ | 1.8 g |
| TPAB | 2.16 g |

| -continued |  |
|---|---|
| Preparation of, for instance, Fe-silicate (Si/Fe = 3200) Catalyst | |
| NaOH | 2.4 g |

*Tetrapropylammonium bromide
**$SiO_2$ 28.9%, $Na_2O$ 9.3

Solutions (A) and (B) are added through microfeeds, respectively, to solution (C) over 10 minutes at pH about 10. The mixture obtained is centrifuged to separate gel from supernatant, the gel is milled for one hour and the milled product is mixed with the supernatant above.

Hydrothermal reaction

A product obtained above is treated in an autoclave with stirring (90 rpm) over 1.5 hours to raise temperature from room temperature to 160° C. The temperature is further raised from 160° C. to 210° C. with rate of 12° C./hour.

Washing, drying and calcining

Washing: water
Drying: 120° C.×24 hours
Calcining: 540° C.×3.5 hours under air stream (100 ml/min.)

Ion exchange treatment

One cycle is 1N $NH_4NO_3$ aq. 80° C.×1 hour, before washing.

After two cycles, the same drying and calcining as above are carried out.

The following examples illustrate the present invention.

The metallosilicate catalyst prepared as above was tableted and then crushed to 10–20 meshes. This catalyst (0.5 g or 2 cc) was packed in a reaction tube (quartz) of 6 mm inner diameter and a mixed gas containing 20 volume % of methanol and 80 volume % of nitrogen was subjected to reaction under the conditions of atmospheric pressure and SV (GHSV) of 2000 $hr^{-1}$-8000 $hr^{-1}$ at prescribed reaction temperatures using an atmospheric flow reaction apparatus.

Components in conversion gas were analyzed by a gas chromatography with an integrator.

Assay conditions for products:

|  | total hydrocarbon | $C_4^-$ hydrocarbon |
|---|---|---|
| Column | Shimazu GC-8APT silicon OV-101 (50 m × 0.2 mm diameter) | Shimazu 7APTF VZ-10 (3 m × 3 mm diameter) |
| Detector | Hydrogen flame ionization detector | Shimazu 7APTF VZ-10 (3 m × 3 mm diameter) |
| Carrier gas | $N_2$ 1.85 $Kg/cm^2$ | $N_2$ 120 ml/min |
| Temperature | From room temperature to 120° C. with raising rate of 4° C./min. | 50° C. |
| Vaporizer temperature | 150° C. | 150° C. |

A. Effects of reaction temperature on production of lower olefins

Reactions were carried out at reaction temperatures of 295° C., 330° C. and 350° C. using the metallosilicate catalyst (atomic ratio of Si/Fe=3200) and relation between reaction temperature and composition of the conversion gas was examined. The results are shown in Table 1.

TABLE 1

| Reaction temperature (°C.) | 295° C. | | 330° C. | | 350° C. | |
|---|---|---|---|---|---|---|
| GHSV ($hr^{-1}$) | 8000 | | 8000 | | 8000 | |
| MeOH concentration (Vol %) | 20 | | 20 | | 20 | |
| Pressure ($Kg/cm^2$) | 1 | | 1 | | 1 | |
| MeOH conversion (C wt %) | After 1 hour | After 3 hours | After 1 hour | After 3 hours | After 1 hour | After 3 hours |
|  | 33.5 | 22.8 | 68.2 | 59.5 | 81.7 | 76.6 |
| HC-selectivity (C wt %) | 51.0 | 59.0 | 86.2 | 80.8 | 95.2 | 91.8 |
| DME selectivity (C wt %) | 49.0 | 41.0 | 13.8 | 19.2 | 4.8 | 8.2 |
| $C_2$–$C_4$ olefins (C wt %) | 97.6 | 95.3 | 60.2 | 62.7 | 60.8 | 60.2 |
| $C_5^+$ Aliphatics (C wt %) | 1.2 | 0.2 | 30.8 | 28.0 | 33.2 | 33.6 |
| Aromatics (C wt %) | — | — | 5.8 | 6.3 | 3.8 | 4.1 |
| STY of $C_2$–$C_4$ olefins (C mol/l · hr) | 11.9 | 9.2 | 25.3 | 21.5 | 33.8 | 30.2 |

HC: Hydrocarbon
DME: Dimethyl ether
STY: Space time yield

Table 1 shows that with increase in reaction temperature, STY (space time yield) of $C_2$–$C_4$ olefins increased.

B. Effects of space velocity on production of lower olefins

Effects of space velocity on production of lower olefins were examined using metallosilicate catalyst (atomic ratio of Si/Fe 3200) at 300° C. and space velocities (GHSV) of 2,000, 4000 and 8000.

The results are shown in Table 2.

TABLE 2

| Reaction temperature (°C.) | 300 | | 300 | | 300 | |
|---|---|---|---|---|---|---|
| GHSV ($hr^{-1}$) | 2000 | | 4000 | | 8000 | |
| MeOH concentration (Vol %) | 20 | | 20 | | 20 | |
| Pressure ($kg/cm^2$) | 1 | | 1 | | 1 | |
| MeOH conversion (C wt %) | After 1 hour | After 3 hours | After 1 hour | After 3 hours | After 1 hour | After 3 hours |
|  | 81.7 | 74.7 | 55.8 | 21.0 | 47.6 | 41.7 |
| HC-selectivity (C wt %) | 92.9 | 85.6 | 58.7 | 53.2 | 61.9 | 56.0 |
| DME selectivity (C wt %) | 7.10 | 14.4 | 41.4 | 46.8 | 38.1 | 44.0 |
| $C_2$–$C_4$ olefin (C wt %) | 51.7 | 52.2 | 76.7 | 89.3 | 87.2 | 96.0 |
| $C_5^+$ aliphatics (C wt %) | 32.6 | 32.2 | 11.4 | 0.67 | 6.3 | 1.3 |

TABLE 2-continued

| | | | | | | |
|---|---|---|---|---|---|---|
| Aromatics (C wt %) | 11.0 | 11.8 | 8.9 | — | 3.0 | 1.0 |
| STY of $C_2$–$C_4$ olefins (C mol/l · hr) | 7.0 | 6.0 | 9.0 | 3.4 | 18.4 | 16.0 |

Table 2 shows that the STY of $C_2$–$C_4$ olefins increases at temperatures within the range of 250°–350° C. as GHSV increases.

C. Effects of Si/Me ratio on production of lower olefins

Effects of Si/Me ratio on production of lower olefins were examined using metallosilicate catalysts (atomic ratios of Si/Ni 400, 3200: Si/Co 40, 3200 and Si/Fe 40, 400) at about 300° C. and space velocities (GHSV) of 2000 and 8000 respectively.

The results are shown in Tables 3 and 4.

Tables 3 and 4 show that hydrocarbon selectivity reaches about 100 % in Fe-silicate catalyst at the temperature of about 300° C.

As described hereinbefore, the metallosilicate catalysts containing metal Fe, Ni or Co prepared above is suitable for synthesis of olefins from methanol. It is assumed to owe to uniformity in crystal structure and acid property of the metallosilicate catalyst.

TABLE 3

| Reaction temperature (°C.) | 291° C. | 291° C. | 291° C. | | 291° C. | |
|---|---|---|---|---|---|---|
| GHSV (hr$^{-1}$) | 8000 | 8000 | 8000 | | 8000 | |
| Si/Me | Si/Ni | Si/Ni | Si/Co | | Si/Fe | |
| | 3200 | 400 | 3200 | 40 | 400 | 40 |
| MeOH concentration (Vol %) | 58.9 | 57.5 | 58.8 | 65.7 | 97.7 | 100 |
| Hydrocarbon selectivity (C wt %) | 39.3 | 34.1 | 51.2 | 80.0 | 99.3 | 100 |
| DME selectivity (C wt %) | 60.7 | 65.9 | 48.8 | 30.6 | 0.7 | 0.0 |
| $C_1$ - hydrocarbon (C wt %) | 4.4 | 4.1 | 4.7 | 5.9 | 0.4 | 0.6 |
| $C_2$–$C_4$ hydrocarbons (C wt %) | 0.0 | 0.0 | 0.0 | 0.8 | 6.7 | 12.8 |
| $C_2^=$–$C_4^=$ hydrocarbons (C wt %) | 91.4 | 91.6 | 91.2 | 88.4 | 55.1 | 38.8 |
| $C_5^+$ aliphatics (C wt %) | 2.6 | 2.8 | 0.3 | 0.3 | 33.6 | 40.7 |
| Aromatics (C wt %) | 1.6 | 1.5 | 3.8 | 4.6 | 4.2 | 7.1 |

TABLE 4

| Reaction temperature (°C.) | 300° C. | 300° C. | 300° C. | | 300° C. |
|---|---|---|---|---|---|
| GHSV (hr$^{-1}$) | 2000 | 2000 | 2000 | | 2000 |
| Si/Me | Si/Ni 3200 | Si/Ni 400 | Si/Co 3200 | 40 | Si/Fe 400 |
| MeOH concentration (Vol %) | 92.8 | 86.6 | 87.8 | 99.8 | 100 |
| Hydrocarbon selectivity (C wt %) | 98.9 | 97.1 | 97.2 | 99.2 | 100 |
| DME selectivity (C wt %) | 1.1 | 2.9 | 2.8 | 0.5 | 0.0 |
| $C_1$ - hydrocarbon (C wt %) | 0.2 | 0.8 | 0.0 | 0.3 | 0.6 |
| $C_2$–$C_4$ hydrocarbons (C wt %) | 4.9 | 6.3 | 3.8 | 4.3 | 10.4 |
| $C_2^=$–$C_4^=$ hydrocarbons (C wt %) | 47.3 | 49.6 | 52.4 | 47.0 | 47.5 |
| $C_5^+$ aliphatics (C wt %) | 35.5 | 37.5 | 33.3 | 36.1 | 27.0 |
| Aromatics (C wt %) | 12.1 | 5.8 | 10.5 | 12.3 | 14.4 |

D. Effects of Me-free catalyst on Production of lower olefins

The Production of the lower olefins was examined using a Me-freesilicate catalyst. Said catalyst was prepared in the similar manner to the above mentioned without metal salt in the solution A.

The result is shown in Table 5.

TABLE 5

| Reaction temperature (°C.) | 300 |
|---|---|
| GHSV (hr$^{-1}$) | 2,000 |
| Metal free catalyst | Silicate |
| MeOH concentration (Vol %) | 100 |
| Hydrocarbon selectivity (C wt %) | 100 |
| DME selectivity (C wt %) | 0 |
| $C_1$ - hydrocarbon (C wt %) | 0.5 |
| $C_2$–$C_4$ hydrocarbon (C wt %) | 14.3 |
| $C_2^=$–$C_4^=$ hydrocarbon (C wt %) | 31.8 |
| $C_5^+$ aliphatics (C wt %) | 33.5 |

TABLE 5-continued

| | |
|---|---|
| Aromatics (C wt %) | 19.9 |

Table 5 shows that productin of the $C_2^=$–$C_4^=$ olefins is smaller than that of the metallosilicate catalyst.

E. Comparison of the present catalyst and the catalyst of DE No. 3215068 (referred to as '068)

| Preparation of the catalyst of DE '068 Si/Fe = 3200 | |
|---|---|
| solution (A) | |
| Fe(NO$_3$)$_2$ 9H$_2$O | 0.04 g |
| H$_2$SO$_4$ | 6.2 g |
| TPAB* | 7.53 g |
| H$_2$O | 60 cc |
| solution (B) | |
| H$_2$O | 45 cc |
| Water Glass (No. 3)** | 69 g |
| solution (C) | |
| H$_2$O | 104 cc |
| NaCl | 26.27 g |

*Tetrapropylammonium bromide
**SiO$_2$ 28.9%, Na$_2$O 9.3%

The solutions (A) and (B) are added to the solution (C) over 10 minutes at pH about 10.

Hydrothermal reaction

The product obtained above is treated in an autoclave with stirring (90 rpm) over 1.5 hours to raise the temperature from a room temperature to 160° C., and the temperature (160° C.) is held for 20 hours. Washing, drying, calcining and ion exchange treatment are effected in the similar manner to that mentioned above.

| Conversion conditions | |
| --- | --- |
| Reaction tube | 6 mm inner diameter quartz |
| Catalyst | 2 cc |
| Feed | Methanol 20% (volume) in $N_2$ gas as a carrier |
| Pressure | atmospheric |

| | the present | DE '068 |
| --- | --- | --- |
| Temperature °C. | 300 | 420 |
| GHSV/hr$^{-1}$ | 2000 | 2000 |

The results are in Table 6.

TABLE 6

| | the present | | | DE '068 |
| --- | --- | --- | --- | --- |
| | Si/Fe = 3200 | Si/Ni = 3200 | Si/Co = 3200 | Si/Fe = 3200 |
| MeOH conversion (c wt %) | 81.7 | 92.8 | 87.8 | 100 |
| Hydrocarbon Selectivity (c wt %) | 92.9 | 98.9 | 97.2 | 15 |
| DMS* Selectivity (c wt %) | 7.1 | 1.1 | 2.8 | 86 |
| Product (c wt %) | | | | |
| $C_2$–$C_4$ olefins | 51.7 | 47.3 | 52.4 | 8.6 |
| $C_5^+$ Aliphatics | 32.6 | 35.5 | 33.3 | 7.2 |
| Aromatics | 11.0 | 12.1 | 10.5 | — |

Selectivity of the present catalyst is superior to that of DE '068.

The present metallosilicate catalyst has acid properties suitable for preparing olefin. The acid properties have two, i.e., weak acid and strong acid. The strong acid property, in particular, attributes to production of olefin. Too strong acidity in the strong acid induces an aromatization or cyclization of dimethyl ether (herein referred to as DME), intermediate, and hydrogen produced reacts with lower olefin to produce lower paraffin. Too low acidity in the strong acid gives no hydrocarbon from DME. Suitable acidity in the strong acid induces production of olefin from DME, and further produces oligomer. Quantitative formation of olefin is effected, because the catalyst has no ability for cyclization and dehydrogenation.

Suitable acidity of the strong acid is attained when metal is Fe, Ni or Co, but too strong acidity when metal is Al. No lower olefin but lower paraffin is obtained when metal is Al as stated above.

The present metallosilicate catalyst has fine and uniform crystals, because the time for preparing catalyst is very short. The fine and uniform crystals making staying time of reaction gas uniform in crystals, until desired olefin is able to produce with high selectivity by controlling conditions. The fines and unformity in crystals improves reaction activity and makes it possible to effect a reaction at lower temperature. Hydrocarbon once produced is not decomposed because the hydrocarbon is not subjected to high temperature. $C_2$ and/or $C_3$ olefin are taken out of the reaction system as soon as they are produced. This favors an improvement in selectivity and in life of catalyst.

Furthermore, process for preparing the present catalyst gives a catalyst a Fe, Ni or Co richcore and an Si-rich coating. Shape selectivity serves to effect no reaction in the coating layer which is non-selective but in the core which has selective.

What is claimed is:

1. A process for conversion of $C_2$–$C_4$ olefinic hydrocarbons from methanol by bringing gaseous methanol into contact with a synthetic metallosilicate catalyst prepared by the following steps:

(1) the first step of preparing a gel mixture by mixing the following solutions (A), (B) and (C); solution (A) being an aqueous solution containing a salt of a metal (Me) of Fe, Ni or Co,. a quaternary alkyl ammonium cation and an inorganic acid; solution (B) being an aqueous silicate solution; solution (C) being an aqueous solution of an ion modifier, the solutions (A) and (B) being added to the solution (C) at a rate such that the pH of the solution (C) is kept at about 10, and the ion modifier has been added to the solution (A) and the quaternary alkyl ammonium cation, the inorganic acid and an alkaline hydroxide have been added to the solution (C) at the time of the addition, (2) the second step of grinding the resulting gel mixture;

(3) the third step of heating the gel mixture to a temperature from room temperature to 150°–190° C. at a constant speed followed by heating to 190°–220° C. at a constant speed or an exponential speed to obtain a precursor synthetic metallosilicate having the following chemical composition in molar ratio;

| Si/Me | 25–3200 |
| --- | --- |
| OH$^-$/SiO$_2$ | 0.3–1.0 |
| H$_2$O/SiO$_2$ | 30–100 |
| R/R + alkali metal | 0.05–0.15 |
| NaCl/H$_2$O | 0.01–0.06 | wherein R is quaternary alkylammonium cation, the alkali metal is sodium or potassium, and Me is Fe, Ni or Co, and (4) the fourth step of calcining the precursor.

2. A process as claimed in claim 1 wherein the salt of metal is a di or tri-valent nitrate, sulfate or chloride of Fe, Ni or Co.

3. A process as claimed in claim 1 wherein R is quaternary $C_{1-3}$ alkyl ammonium cation.

4. A process as claimed in claim 1 wherein R is quaternary propyl ammonium cation.

5. A process as claimed in claim 1, wherein the ion modifier is sodium chloride.

6. A process as claimed in claim 1, wherein, after the third step, the precurser synthetic metallosilicate is washed, dried and calcined, and, after calcination, dipped in an aqueous solution of $NH_4NO_3$, washed, dried and calcined.

7. A process as claimed in claim 1, wherein the methanol is brought into contact with the catalyst at a temperature of 250°–400° C.

8. A process as claimed in claim 6 wherein said contact is carried out at a space velocity of 2000–8000 hr$^{-1}$ and a pressure of atmospheric pressure $-50$ kg/cm$^2$.

9. A process, as claimed in claim 7 wherein the methanol is brought into contact with the catalyst at a reaction temperature of 280°–350° C.

10. A process, as claimed in claim 1 wherein the metallosilicate catalyst consists of fine, uniform crystals.

11. A process, as claimed in claim 10 wherein the metallosilicate catalyst consists of fine, uniform crystals.

12. A process, as in claim 1 wherein the catalyst has a Fe, Ni or Co rich core and a Si-rich coating.

13. A process, as in claim 12, wherein the metallosilicate catalyst consists of fine, uniform crystals.

14. A process, as in claim 1 wherein the yield of olefins is 51.7–97.6%.